(12) United States Patent
Doods et al.

(10) Patent No.: US 6,521,609 B1
(45) Date of Patent: *Feb. 18, 2003

(54) USE OF CGRP ANTAGONISTS AND CGRP RELEASE INHIBITORS FOR COMBATING MENOPAUSAL HOT FLUSHES

(75) Inventors: Henri Doods, Warthausen (DE); Klaus Rudolf, Warthausen (DE); Wolfgang Eberlein, Biberach (DE); Wolfhard Engel, Biberach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/614,343

(22) Filed: Jul. 12, 2000

Related U.S. Application Data
(60) Provisional application No. 60/184,800, filed on Feb. 24, 2000.

(30) Foreign Application Priority Data

Aug. 10, 1999 (DE) ......................... 199 37 304

(51) Int. Cl.⁷ ..................... A61K 31/454; A61K 31/55; A61K 31/53; C07D 223/00; C07D 211/00
(52) U.S. Cl. ..................... 514/183; 514/212; 514/218; 514/241; 514/247; 514/277; 514/316; 514/331; 540/454; 544/215; 546/184
(58) Field of Search ................. 514/183, 212, 514/241, 218, 247, 277, 316, 331

(56) References Cited

U.S. PATENT DOCUMENTS 5,910,482 A   6/1999   Yallampalli et al.
6,313,097 B1 * 11/2001 Eberlein et al. ............ 514/183

FOREIGN PATENT DOCUMENTS

DE   19911039 A1   9/2000
EP   0821061 A2    1/1998
WO   98/11128 A1   3/1998

OTHER PUBLICATIONS

XP–000992559; Doods et al; "Pharmacological profile of BIBN4096BS, the first selective small molecule CGRP antagonist,"; Brisith Journal of Pharmacology; (2000); 129; 420–423.

* cited by examiner

Primary Examiner—Theodore J. Criares
(74) Attorney, Agent, or Firm—Robert P. Raymond; Timothy X. Witkowski; Mary-Ellen Devlin

(57) ABSTRACT

A method for treating menopausal hot flushes using CGRP antagonists and/or CGRP release inhibitors and the corresponding pharmaceutical compositions containing as active substance one or more CGRP antagonists and/or CGRP release inhibitors, and the preparation thereof.

13 Claims, No Drawings

USE OF CGRP ANTAGONISTS AND CGRP RELEASE INHIBITORS FOR COMBATING MENOPAUSAL HOT FLUSHES

RELATED APPLICATION

This application claims benefit of U.S. Provisional Application No. 60/184,800, filed Feb. 24, 2000.

BACKGROUND OF THE INVENTION

Hot flushes are a common symptom of peri/post-menopausal syndrome the physiology of which is still not fully understood. Apart from hormone replacement therapy, which is a complex intervention and frequently cannot be used long-term owing to its side effects, there has up until now been no simple therapy largely free from side effects for this generally troublesome condition.

Hot flushes are caused by vasodilatation and increased blood flow. A number of publications have mentioned the possibility that CGRP (calcitonin gene-related peptide) plays a part in the occurrence of menopausal hot flushes in oestrogen-deficient women owing to the vasodilatory properties of this neuropeptide ([1]: J. Endocrinol. (1995), 146 (3), 431–437; [2]: Acta Physiol. Scand. (1998), 162(4), 517–522; [3]: Am. J. Obstet. Gynecol. (1996), 175(3, Pt. 1), 638–642). The therapeutic use of CGRP antagonists for treating menopausal syndrome has not previously been proposed in the literature.

It has now been found that the symptoms of menopausal hot flushes can be effectively prevented or their distressing effects substantially alleviated by substances which antagonize the effects of CGRP (CGRP antagonists) or inhibit or reduce the release of CGRP from sensory nerve endings (CGRP release inhibitors), this therapeutic approach being superior to hormone replacement therapy in particular because of its lack of side effects.

SUMMARY OF THE INVENTION

The present invention thus relates to the use of CGRP antagonists and/or CGRP release inhibitors for combating menopausal hot flushes, including both prevention and acute treatment. The use according to the invention preferably comprises monotherapy with a single substance, but also includes combined therapy with a number of substances from the specified groups of active substances. Moreover, the treatment according to the invention may be carried out in addition to conventional hormone replacement therapy.

The invention also relates to the use of CGRP antagonists and/or CGRP release inhibitors for preparing a pharmaceutical composition for treating menopausal hot flushes as well as the corresponding pharmaceutical compositions containing as active substance one or more CGRP antagonists and/or CGRP release inhibitors.

Any pharmaceutically acceptable active substances which antagonize the known effects of CGRP or inhibit the release of CGRP from sensory nerve endings may be used for the purposes of the present invention.

DETAILED DESCRIPTION OF THE INVENTION

Examples of CGRP antagonists include the amino acid derivatives described in WO 98/11128 or DE 199 11 039, as well as the non-peptidic active substances described in WO 98/56779, WO 98/09630, and WO 97/09046.

Examples of CGRP release inhibitors include serotonin 5-$HT_{1D}$-agonists such as avitriptan, eletriptan, naratriptan, rizatriptan, sumatriptan or zolmitriptan, as well as 5-$HT_{1F}$-agonists or NPY-agonists.

Of the CGRP antagonists described in WO 98/11128, the following compounds, for example, may be used for the treatment of menopausal hot flushes, for the preparation of a corresponding pharmaceutical composition and as an ingredient of a corresponding pharmaceutical composition:

(A) 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine, (B) 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine, (C) 1-[$N^2$-[4-amino-3,5-dibromo-N-[[4-(3,4-dihydro-2(1H)-oxoquinazolin-3-yl)-1-piperidinyl]carbonyl]-D-phenylalanyl]-L-lysyl]-4-(4-pyridinyl)-piperazine, (D) 1-[$N^2$-[4-amino-3,5-dibromo-N-[[4-(3,4-dihydro-2(1H)-oxoquinazolin-3-yl)-1-piperidinyl]carbonyl]-D-phenylalanyl]-L-lysyl]-4-(4-pyridinyl)-piperidine, (E) 1-[$N^2$-[3,5-dibromo-N-[[4-(1,3-dihydro-4-phenyl-2(2H)-oxoimidazol-1-yl)-1-piperidinyl]carbonyl]-D-tyrosyl]-L-lysyl]-4-(4-pyridinyl)-piperazine, (F) 1-[$N^2$-[4-amino-3,5-dibromo-N-[[4-(1,3-dihydro-4-phenyl-2(2H)-oxoimidazol-1-piperidinyl]carbonyl]-D-phenyl-alanyl]-L-lysyl]-4-(4-pyridinyl)-piperazine, (G) 1-[3,5-dibromo-N-[[4-(3,4-dihydro-2(1H)-oxothieno[3,4-d]pyrimidin-3-yl)-1-piperidinyl]carbonyl]-D-tyrosyl]-4-(1-piperidinyl)-piperidine, (H) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-methyl-4-piperidinyl)-piperidine, (I) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-piperidinyl)-piperidine, (J) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-methyl-4-piperidinyl)-piperazine, (K) 1-[4-amino-3,5-dibromo-N-[[4-(3,4-dihydro-2(1H)-oxothieno[3,2-d]pyrimidin-3-yl)-1-piperidinyl]carbonyl]-D-phenylalanyl]4-(1-piperidinyl)-piperidine, L) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-ethyl-4-piperidinyl)-piperidine, (M) 1-[4-amino-3,5-dibromo-N-[[4-[3,4-dihydro-2(1H)-oxoquinazolin-3-yl]-1-piperidinyl]carbonyl]-D-phenylalanyl]-4-(1-hexyl-4-piperidinyl)-piperidine, (N) 1-[4-amino-3,5-dibromo-N-[[4-[3,4-dihydro-2(1H)-oxoquinazolin-3-yl]-1-piperidinyl]carbonyl]-D-phenylalanyl]-4-(1-cyclopropylmethyl-4-piperidinyl)-piperidine, (O) 1-[N-[[4-[3,4-dihydro-2(1H)-oxoquinazolin-3-yl]-1-piperidinyl]carbonyl]-3-ethenyl-D,L-phenylalanyl]-4-(hexahydro-1H-1-azepinyl)-piperidine, (P) (R,S)-1-[4-[4-(3,4-dihydro-2(1H)-oxoquinazolin-3-yl)-1-piperidinyl]-2-[(4-hydroxy-3,5-dimethylphenyl)methyl]-1,4-dioxobutyl]-4-(1-piperidinyl)-piperidine, (Q) 1-[4-amino-3,5-dibromo-N-[[4-[N-(aminocarbonyl)-N-phenylamino]-1-piperidinyl]carbonyl]-D-phenylalanyl]-4-(1-piperidinyl)-piperidine, (R) 1-[4-amino-3,5-dibromo-N-[[4-(3,4-dihydro-2(1H)-oxoquinazolin-3-yl)-1-piperidinyl]carbonyl]-D-phenylalanyl]-4-(5-methoxy-4-pyrimidinyl)-piperazine, (S) 1-[4-amino-3,5-dibromo-N-[[4-(1,1-dioxido-3(4H)-oxo-1,2,4-benzothiadiazin-2-yl)-1-piperidinyl]carbonyl]-D-phenylalanyl]-4-(1-piperidinyl)-piperidine, (T) 1-[4-amino-3,5-dibromo-N-[[4-[2(1H)-oxoquinolin-3-yl]-1-piperidinyl]carbonyl]-D-phenylalanyl]-4-(1-piperidinyl)-piperidine, (U) 1-[4-amino-3,5-dibromo-N-[[4-[3,4-dihydro-2(1H)-oxoquinazolin-3-yl]-1-piperidinyl]carbonyl]-D-phenylalanyl]-4-[3-(dimethylamino)propyl]-piperazine, V) 1-[4-amino-3,5-dibromo-N-[[4-[3,4-dihydro-2(1H)-oxoquinazolin-3-yl]-1-piperidinyl]carbonyl]-D-phenylalanyl]-4-(4-methyl-1-piperazinyl)-piperidine, (W) 1-[4-amino-3,5-dibromo-N-[[4-[3,4-dihydro-2(1H)-oxoquinazolin-3-yl]-1-piperidinyl]carbonyl]-D-phenylalanyl]-4-[(1-methyl-4-piperidinyl)carbonyl]-piperazine, (X) 1-[4-amino-3,5-dibromo-N-[[4-[3,4-dihydro-2(1H)-oxoquinazolin-3-yl]-1-piperidinyl]carbonyl]-D-phenylalanyl]-4-[(1-methyl-4-piperazinyl)carbonyl]-piperazine, (Y) 1-[4-amino-3,5-dibromo-N-[[4-(3,4-dihydro-2(1H)-oxoquinazolin-3-yl)-1-piperidinyl]carbonyl]-D-phenylalanyl]-4-[4-[4-(dimethylamino)butyl]phenyl]-piperazine, (Z) 1-[4-amino-3,5-dibromo-N-[[4-(3,4-dihydro-2(1H)-oxoquinazolin-3-yl)-1-piperidinyl]carbonyl]-D-phenylalanyl]-4-[4-(dimethylamino)-1-piperidinyl]-piperidine, (AA) 1-[$N^2$-[[4-(1,3-dihydro-4-phenyl-2(2H)-oxoimidazol-1-yl)-1-piperidinyl]carbonyl]-N'-methyl-D-tryptyl]-4-(4-methyl-1-piperazinyl)-piperidine, (AB) 1-[$N^2$-[[4-(1,3-dihydro-4-phenyl-2(2H)-oxoimidazol-1-yl)-1-piperidinyl]carbonyl]-N'-(1,1-dimethylethoxycarbonyl)-D-tryptyl]-4-(1-methyl-4-piperidinyl)-piperidine, (AC) (R,S)-1-[4-[4-(3,4-dihydro-2(1H)-oxoquinazolin-3-yl)-1-piperidinyl]-2-[(3,5-dibromo-4-methylphenyl)methyl]-1,4-dioxobutyl]-4-(4-methyl-1-piperazinyl)-piperidine, (AD) (R,S)-1-[4-[4-(3,4-dihydro-2(1H)-oxoquinazolin-3-yl)-1-piperidinyl]-2-[(3,5-dibromo-4-methoxyphenyl)methyl]-1,4-dioxobutyl]-4-(1-methyl-4-piperidinyl)-piperidine, (AE) (R,S)-1-[4-[4-(3,4-dihydro-2(1H)-oxoquinazolin-3-yl)-1-piperidinyl]-2-[(3,4-dibromphenyl)methyl]-1,4-dioxobutyl]-4-(4-methyl-1-piperazinyl)-piperidine, (AF) 1-[$N^2$-[N-[[4-(1,3-dihydro-2(2H)-oxobenzimidazol-1-yl)-1-piperidinyl]carbonyl]-3,5-dibromo-D-tyrosyl]-L-lysyl]-4-(4-pyridinyl)-piperazine, (AG) 1-[4-amino-3,5-dibromo-N-[[4-(1,3-dihydro-6-hydroxy-2(2H)-oxobenzimidazol-1-yl)-1-piperidinyl]carbonyl]-D-phenylalanyl]-4-(1-piperidinyl)-piperidine, (AH) 1-[$N^2$-[4-amino-3,5-dibromo-N-[[4-(1,3-dihydro-2(2H)-oxobenzimidazol-1-yl)-1-piperidinyl]carbonyl]-D-phenylalanyl]-$N^{6,N^6}$-dimethyl-L-lysyl]-4-(4-pyridinyl)-piperazine, (AI) 1-[$N^2$-[4-amino-3,5-dibromo-N-[[4-(3,4-dihydro-2(1H)-oxoquinazolin-3-yl)-1-piperidinyl]carbonyl]-D-phenylalanyl]-$N^{6,N^6}$-dimethyl-L-lysyl]-4-(4-pyridinyl)-piperazine, (AJ) (R,S)-1-[2-(4-amino-3,5-dibromobenzoyl)-4-[4-(3,4-dihydro-2(1H)-oxoquinazolin-3-yl)-1-piperidinyl]-4-oxobutyl]-4-(1-piperidinyl)-piperidine, (AK) 1-[4-amino-3,5-dibromo-N-[[4-(3,4-dihydro-2,2-dioxido-2,1,3-benzothiadiazin-3-yl)-1-piperidinyl]carbonyl]-D-phenylalanyl]-4-(1-piperidinyl)-piperidine, (AL) 1-[4-amino-3,5-dibromo-N-[[4-[1,3-dihydro-2(2H)-oxoimidazo[4,5-c]quinolin-3-yl]-1-piperidinyl]carbonyl]-D-phenyl-alanyl]-4-(1-piperidinyl)carbonyl]-piperidine (AM) 1-[4-amino-3,5-dibromo-N-[[4-(3,4-dihydro-2(1H)-oxoquinazolin-3-yl)-1-piperidinyl]carbonyl]-D-phenylalanyl]-4-(1-piperidinyl)-piperidine, (AN) 1-[$N^2$-[3,5-dibromo-N-[[4-(3,4-dihydro-2(1H)-oxoquinazolin-3-yl)-1-piperidinyl]carbonyl]-D-tyrosyl]-$N^6,N^6$-dimethyl-L-lysyl]-4-(4-pyridinyl)-piperazine, (AO) 1-[4-amino-N-[[4-[4-(3-bromophenyl)-1,3-dihydro-2(2H)-oxoimidazol-1-yl]-1-piperidinyl]carbonyl]-3,5-dibromo-D-phenylalanyl]-4-(1-methyl-4-piperidinyl)-piperidine, (AP) 1-[4-amino-3,5-dibromo-N-[[4-[1,3-dihydro-4-phenyl-2(2H)-oxoimidazol-1-yl]-1-piperidinyl]carbonyl]-D-phenylalanyl]-4-(4-methyl-1-piperazinyl)-piperidine, (AQ) 1-[4-amino-3,5-dibromo-N-[[4-[1,3-dihydro-4-[3-(trifluoromethyl)phenyl]-2-(2H)-oxoimidazol-1-yl]-1-piperidinyl]carbonyl]-D-phenylalanyl]-4-(1-piperidinyl)-piperidine, (AR) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(exo-8-methyl-8-azabicyclo[3,2,1]oct-3-yl)-piperazine, (AS) 1-[3,5-dibromo-N-[[4-(1,3-dihydro-4-phenyl-2(2H)-oxoimidazol-1-yl)-1-piperidinyl]carbonyl]-D-tyrosyl]-4-(1-piperidinyl)-piperidine, (AT) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-ethyl-4-piperidinyl)-piperazine, (AU) 1-[4-amino-3,5-dibromo-N-[[4-[1,3-dihydro-4-phenyl-2(2H)-oxoimidazol-1-yl]-1-piperidinyl]carbonyl]-D-phenylalanyl]-4-(hexahydro-4-methyl-1H-1,4-diazepin-1-yl)-piperidine, (AV) 1-[3,5-dibromo-N-[[4-(3,4-dihydro-2(1H)-oxoquinazolin-3-yl)-1-piperidinyl]carbonyl]-D-tyrosyl]-4-[1-(methylsulfonyl)-4-piperidinyl]-piperidine, (AW) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(1-methyl-4-piperidinyl)-piperidine, (AX) 1-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(hexahydro-1H-1-azepinyl)-piperidine, (AY) 1-[3,5-dibromo-N-[[4-(3,4-dihydro-2(1H)-oxoquinazolin-3-yl)-1-piperidinyl]carbonyl]-D-tyrosyl]-4-(1-methyl-4-piperidinyl)-piperidine, (AZ) 1-[4-amino-3,5-dibromo-N-[[4-(3,4-dihydro-2(1H)-oxoquinazolin-3-yl)-1-piperidinyl]carbonyl]-D- phenylalanyl]-4-(exo-8-methyl-8-azabicyclo[3,2,1]oct-3-yl)-piperazine, (BA) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(1-methyl-4-piperidinyl)-piperazine, (BB) 1-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(1-piperidinyl)-piperidine, (BC) 1-[$N^6$-acetyl-$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine, (BD) 1-[3,5-dibromo-N-[[4-(1,3-dihydro-4-phenyl-2(2H)-oxoimidazol-1-yl)-1-piperidinyl]carbonyl]-D-tyrosyl]-4-(hexahydro-1H-1-azepinyl)-piperidine, (BE) 1-[4-amino-3,5-dibromo-N-[[4-(1,3-dihydro-4-(3-thienyl)-2(2H)-oxoimidazol-1-yl)-1-piperidinyl]carbonyl]-D-phenyl-alanyl]-4-(1-methyl-4-piperidinyl)-piperidine, (BF) 1-[4-amino-3,5-dibromo-N-[[4-[1,3-dihydro-4-[3-(trifluoromethyl)phenyl]-2H)-oxoimidazol-1-yl]-1-piperidinyl]carbonyl]-D-phenylalanyl]-4-(1-methyl-4-piperidinyl)-piperidine, (BG) 1-[3,5-dibromo-N-[[4-(3,4-dihydro-2(1H)-oxoquinazolin-3-yl)-1-piperidinyl]carbonyl]-D-tyrosyl]-4-[1-(hydroxycarbonylmethyl)-4-piperidinyl]-piperidine, (BH) 1-[4-amino-3,5-dibromo-N-[[4-[3,4-dihydro-2(1H)-oxoquinazolin-3-yl]-1-piperidinyl]carbonyl]-D-phenylalanyl]-4-(1-methylsulphonyl-4-piperidinyl)-piperidine, (BI) 1-[3,5-dibromo-N-[[4-(3,4-dihydro-2(1H)-oxoquinazolin-3-yl)-1-piperidinyl]carbonyl]-D-tyrosyl]-4-(4-piperidinyl)-piperidine, (BJ) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(1-ethyl-4-piperidinyl)-piperidine, (BK) 1-[4-amino-3,5-dibromo-N-[[4-(1,3-dihydro-4-(3-hydroxyphenyl)-2(2H)-oxoimidazol-1-yl)-1-piperidinyl]carbonyl]-D-phenylalanyl]-4-(1-methyl4-piperidinyl)-piperidine, (BL) 1-[3,5-dibromo-N-[[4-(3,4-dihydro-2(1H)-oxoquinazolin-3-yl)-1-piperidinyl]carbonyl]-D-tyrosyl]-4-(hexahydro-1H-1-azepinyl)-piperidine, (BM) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(1-piperidinyl)-piperidine, (BN) 1-[4-amino-3,5-dibromo-N-[[4-[4-(3-bromophenyl)-1,3-dihydro-2(2H)-oxoimidazol-1-yl]-1-piperidinyl]carbonyl]-D-phenylalanyl]-4-(exo-8-methyl-8-azabicyclo[3,2,1]oct-3-yl)-piperazine, (BO) 1-[4-amino-3,5-dibromo-N-[[4-(3,4-dihydro-2(1H)-oxoquinazolin-3-yl)-1-piperidinyl]carbonyl]-D-phenylalanyl]-4-(1-ethyl-4-piperidinyl)-piperidine, (BP) 1-[4-amino-3,5-dibromo-N-[[4-(3,4-dihydro-2(1H)-oxoquinazolin-3-yl)-1-piperidinyl]carbonyl]-D-phenylalanyl]-4-(1-ethyl-4-piperidinyl)-piperazine, (BQ) 1-[4-amino-3,5-dibromo-N-[[4-[1,3-dihydro-4-(3-methoxyphenyl)-2(2H)-oxoimidazol-1-yl]-1-piperidinyl]carbonyl]-D-phenylalanyl]-4-(exo-8-methyl-8-azabicyclo[3,2,1]oct-3-yl)-piperazine, (BR) 1-[3,5-dibromo-N-[[4-(3,4-dihydro-2(1H)-oxoquinazolin-3-yl)-1-piperidinyl]carbonyl]-D-tyrosyl]-4-[1-(cyclopropyl-methyl)-4-piperidinyl]-piperidine, (BS) 1-[4-amino-3,5-dibromo-N-[[4-(3,4-dihydro-2(1H)-oxoquinazolin-3-yl)-1-piperidinyl]carbonyl]-D-phenylalanyl]-4-(hexahydro-1H-1-azepinyl)-piperidine, (BT) 1-[4-amino-3,5-dibromo-N-[[4-(3,4-dihydro-2(1H)-oxoquinazolin-3-yl)-1-piperidinyl]carbonyl]-D-phenylalanyl]-4-(4-piperidinyl)-piperidine, (BU) 1-[3,5-dibromo-N-[[4-(1,3-dihydro-4-phenyl-2(2H)-oxoimidazol-1-yl)-1-piperidinyl]carbonyl]-D-tyrosyl]-4-(4-pyridinyl)-piperidine, (BV) 1-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(1-methyl-4-piperidinyl)-piperazine, (BW) 1-[$N^2$-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-L-lysyl]-4-(4-pyridinyl)-piperazine, (BX) 1-[3,5-dibromo-N-[[4-(1,3-dihydro-4-(3-thienyl)-2(2H)-oxoimidazol-1-yl)-1-piperidinyl]carbonyl]-D-tyrosyl]-4-(1-piperidinyl)-piperidine, (BY) 1-[4-amino-N-[[4-[4-(3-chlorophenyl)-1,3-dihydro-2(2H)-oxoimidazol-1-yl]-1-piperidinyl]carbonyl]-3,5-dibromo-D-phenylalanyl]-4-(1-methyl-4-piperidinyl)-piperidine, (BZ) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(hexahydro-1H-1-azepinyl)-piperidine, (CA) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-methyl-4-piperidinyl)-piperazine, (CB) 1-[4-amino-N-[[4-[4-(3-chlorophenyl)-1,3-dihydro-2(2H)-oxoimidazol 1-yl]-1-piperidinyl]carbonyl]-3,5-dibromo-D-phenylalanyl]-4-(hexahydro-1H-1-azepinyl)-piperidine, (CC) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(4-pyridinyl)-piperazine, (CD) 1-[3,5-dibromo-N-[[4-(1,3-dihydro-4-phenyl-2(2H)-oxoimidazol-1-yl)-1-piperidinyl]carbonyl]-D-tyrosyl]-4-(1-methyl-4-piperidinyl)-piperidine, (CE) 1-[4-amino-3,5-dibromo-N-[[4-[1,3-dihydro-4-phenyl-2(2H)-oxoimidazol-1-piperidinyl]carbonyl]-D-phenylalanyl]-4-[4-(1-oxoethyl)phenyl]-piperazine, (CF) 1-[3,5-dibromo-N-[[4-[3,4-dihydro-2(1H)-oxoquinazolin-3-yl]-1-piperidinyl]carbonyl]-D-tyrosyl]-4-(1-methyl-4-piperidinyl)-piperazine, (CG) 1-[4-amino-3,5-dibromo-N-[[4-[1,3-dihydro-4-(3-nitrophenyl)-2(2H)-oxoimidazol-1-yl]-1-piperidinyl]carbonyl]-D-phenylalanyl]-4-(1-methyl-4-piperidinyl)-piperidine, (CH) 1-[4-amino-3,5-dibromo-N-[[4-[3,4-dihydro-2(1H)-oxoquinazolin-3-yl]-1-piperidinyl]carbonyl]-D-phenylalanyl]-4-(1-pyrrolidinyl)-piperidine, (CI) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(hexahydro-1H-1-azepinyl)-piperidine and (CJ) 1-[4-amino-3,5-dibromo-N-[[4-(1,3-dihydro-4-(3-thienyl)-2(2H)-oxoimidazol-1-yl)-1-piperidinyl]carbonyl]-D-phenyl-alanyl]-4-(1-methyl-4-piperidinyl)-piperazine, the tautomers, the diastereomers, the enantiomers, the mixtures thereof and the physiologically acceptable salts thereof.

The following compounds are preffered:

(A) 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine, (B) 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine, (I) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-piperidinyl)-piperidine, (J) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-methyl-4-piperidinyl)-piperazine, (AC) (R,S)-1-[4-[4-(3,4-dihydro-2(1H)-oxoquinazolin-3-yl)-1-piperidinyl]-2-[(3,5-dibromo-4-methylphenyl)methyl]-1,4-dioxobutyl]-4-(4-methyl-1-piperazinyl)-piperidine, (AF) 1-[$N^2$-[N-[[4-(1,3-dihydro-2(2H)-oxobenzimidazol-1-yl)-1-piperidinyl]carbonyl]-3,5-dibromo-D-tyrosyl]-L-lysyl]-4-(4-pyridinyl)-piperazine, and (AM) 1-[4-amino-3,5-dibromo-N-[[4-(3,4-dihydro-2(1H)-oxoquinazolin-3-yl)-1-piperidinyl]carbonyl]-D-phenylalanyl]-4-(1-piperidinyl)-piperidine, the tautomers, the diastereomers, the enantiomers, the mixtures thereof and the physiologically acceptable salts thereof.

The following compounds are particularly preferred:

(A) 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine; and (B) 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine, the tautomers, the diastereomers, the enantiomers, the mixtures thereof and the physiologically acceptable salts thereof.

The dosage required to produce the desired effect is appropriately 0.0001 to 3 mg/kg of body weight, preferably 0.01 to 1 mg/kg of body weight for intravenous or subcutaneous administration and 0.01 to 10 mg/kg of body weight, preferably 0.1 to 10 mg/kg of body weight for administration by oral or nasal route or by inhalation, 1 to 3 times a day in each case.

If the treatment with CGRP antagonists and/or CGRP release inhibitors is given as a supplement to conventional hormone replacement therapy, it is advisable to reduce the doses given above, and in this case the dosage may range from 1/5 of the lower limits specified above up to 1/1 of the upper limits specified above.

For this purpose, the CGRP antagonists and/or CGRP release inhibitors may be formulated with one or more conventional inert carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propylene glycol, cetylstearyl alcohol, carboxymethylcellulose or fatty substances such as hard fat or suitable mixtures thereof in conventional galenic preparations such as plain or coated tablets, capsules, powders, suspensions, solutions, metering aerosols or suppositories.

Preparations which are particularly suitable for treating menopausal hot flushes are those which contain one of the active substances:

(A) 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine, (B) 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine, (I) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-piperidinyl)-piperidine, (J) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl-4-(1-methyl-4-piperidinyl)-piperazine, (AC) (R,S)-1-[4-[4-(3,4-dihydro-2(1H)-oxoquinazolin-3-yl)-1-piperidinyl]-2-[(3,5-dibromo-4-methylphenyl)methyl]-1,4-dioxobutyl]-4-(4-methyl-1-piperazinyl)-piperidine, (AF) 1-[$N^2$-[N-[[4-(1,3-dihydro-2(2H)-oxobenzimidazol-1-yl)-1-piperidinyl]carbonyl]-3,5-dibromo-D-tyrosyl]-L-lysyl]-4-(4-pyridinyl)-piperazine, or (AM) 1-[4-amino-3,5-dibromo-N-[[4-(3,4-dihydro-2(1H)-oxoquinazolin-3-yl)-1-piperidinyl]carbonyl]-D-phenylalanyl]-4-(1-piperidinyl)-piperidine, in one of the following pharmaceutical formulations:

capsules for powder inhalation containing 1 mg of active substance, preferably active substance (A) or (B), inhalable solution for nebulisers containing 1 mg of active substance, preferably active substance (A) or (B), propellant gas-operated metering aerosol containing 1 mg of active substance, preferably active substance (A) or (B), nasal spray containing 1 mg of active substance, preferably active substance (A) or (B), tablets containing 20 mg of active substance, preferably active substance (B), capsules containing 20 mg of active substance, preferably active substance (B), aqueous solution for nasal application containing 10 mg of active substance, preferably active substance (A) or (B), aqueous solution for nasal application containing 5 mg of active substance, preferably active substance (A) or (B), or suspension for nasal application containing 20 mg of active substance, preferably active substance (A) or (B).

CGRP is released by sensory nerves, e.g., the trigeminal nerve which innervates part of the skin of the face. It has already been shown that stimulation of the trigeminal ganglion in humans leads to an increase in the CGRP plasma level and causes reddening of the face ([4]: P. J. Goadsby et al., Annals of Neurology, Vol. 23, No. 2,1988, 193–196,).

To demonstrate that hot flushes can be successfully treated using CGRP antagonists and CGRP release inhibitors, an increased release of endogenous CGRP was induced in marmosets by stimulating the trigeminal ganglion, leading to increased blood flow through the blood vessels of the skin. The efficacy of the following test substances was characterised by determining the dose administered i.v. which reduces by 50% the increased blood flow through the skin of the face which has been brought about by endogenous CGRP:

(A) is 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine, (B) is 1-[4-amino-3,5-dibromo-N-[[4-(2,3,4,5-tetrahydro-2(M11)-oxo-1,3-benzodiazepin-3-yl)-1-piperidinyl]carbonyl]-D-phenylalanyl]-4-(1-piperidinyl)-piperidine, (AC) is (R,S)-1-[4-[4-(3,4-dihydro-2(1H)-oxoquinazolin-3-yl)-1-piperidinyl]-2-[(3,5-dibromo-4-methylphenyl)methyl]-1,4-dioxobutyl]-4-(4-methyl-1-piperazinyl)-piperidine, (AM) is 1-[4-amino-3,5-dibromo-N-[[4-(3,4-dihydro-2(1H)-oxoquinazolin-3-yl)-1-piperidinyl]carbonyl]-D-phenylalanyl]-4-(1-piperidinyl)-piperidine, (DA) is sumatriptan, and (DB) is zolmitriptan.

Description of the Method

Marmosets of both sexes (300–400 g) are anaesthetized with pentobarbital (initially with 30 mg/kg, i.p., followed by infusion of 6 mg/kg/h, i.m.). The body temperature is maintained at 37° C. using a heating plate. Pancuronium is administered as a muscle relaxant (initially 1 mg/kg, 0.5 mg after each hour thereafter). The animal's head is secured in a stereotactical apparatus. After the skin on the head has been opened using a lengthwise incision, a small hole is drilled in the skull and a bipolar electrode (Rhodes SNES 100) is lowered into the trigeminal ganglion. Locating the ganglion is made easier by the use of an X-ray which shows up the bone structure of the skull. The petrous bone serves as a guide for placing the electrode (CCX-Digital X-ray apparatus). The position of the electrode in the ganglion is monitored at the end of each experiment. The stimulation parameters are: 10 Hz, 2 mA, 2 msec, for 30 seconds. The blood flow in the micro-vessels of the facial skin is determined by laser Doppler flow measurement using a PeriFlux Laser Doppler System. The animals are exposed to 2 to 3 stimulation periods at intervals of 30 minutes in each case. The first stimulation serves as a reference value for the other stimulations. The test substances are administered i.v. 5 minutes before the 2nd and 3rd stimulation periods.

TABLE 1

| Substance | 50% dose |
| --- | --- |
| A | 0.003 mg/kg |
| B | 0.042 mg/kg |
| AC | 0.018 mg/kg |
| AM | 0.046 mg/kg |
| DA | 0.280 mg/kg |
| DB | 0.035 mg/kg |

TABLE 1-continued

| Substance | 50% dose |
| --- | --- |

"50% dose" is an i.v. dose which reduces by 50% the increased blood flow through the facial skin caused by endogenous CGRP The Examples which follow describe pharmaceutical preparations which contain as active substance a CGRP antagonist or CGRP release inhibitor for use according to the invention, preferably one of the amino acid derivatives described in WO 98/11128 or DE 199 11 039, for example one of the abovementioned active substances (A) or (B):

EXAMPLE I

Capsules for Powder Inhalation with 1 mg of Active Substance (A) or (B)

Composition:

1 capsule for powder inhalation contains:

| active substance (A) or (B) | 1.0 mg |
| --- | --- |
| lactose | 20.0 mg |
| hard gelatine capsules | 50.0 mg |
| | 71.0 mg |

Method of Preparation

The active substance is ground to the particle size needed for inhalation. The ground active substance is homogeneously mixed with the lactose. The mixture is packed into hard gelatine capsules.

EXAMPLE II

Inhalable Solution for Respimat® with 1 mg of Active Substance (A) or (B)

Composition:

1 spray contains:

| active substance (A) or (B) | 1.0 mg |
| --- | --- |
| benzalkonium chloride | 0.002 mg |
| disodium edetate | 0.0075 mg |
| purified water | ad 15.0 µl |

Method of Preparation

The active substance and benzalkonium chloride are dissolved in water and packed in Respimate® cartridges.

EXAMPLE III

Inhalable Solution for Nebulisers with 1 mg of Active Substance (A) or (B)

Composition: 1 vial contains:

| active substance (A) or (B) | 0.1 g |
| --- | --- |
| sodium chloride | 0.18 g |
| benzalkonium chloride | 0.002 g |
| purified water | ad 20.0 ml |

Method of Preparation

Active substance, sodium chloride and benzalkonium chloride are dissolved in water.

EXAMPLE IV

Propellant Gas-operated Metering Aerosol with 1 mg of Active Substance (A) or (B)

Composition:

1 spray contains:

| | | |
|---|---|---|
| active substance (A) or (B) | 1.0 mg | |
| lecithin | 0.1 % | |
| propellant gas | ad 50.0 µl | |

Method of Preparation

The micronised active substance is homogeneously suspended in the mixture of lecithin and propellant gas. The suspension is transferred into a pressurised container with a metering valve.

EXAMPLE V

Nasal Spray with 1 mg of Active Substance (A) or (B)

Composition:

1 spray jet contains

| | | |
|---|---|---|
| active substance (A) or (B) | 1.0 mg | |
| mannitol | 5.0 mg | |
| disodium edetate | 0.05 mg | |
| ascorbic acid | 1.0 mg | |
| purified water | ad 0.1 ml | |

Method of Preparation

The active substance and the excipients are dissolved in water and transferred into a suitable container.

EXAMPLE VI

Injectable Solution with 5 mg of Active Substance (A) or (B) per 5 ml

Composition:

| | |
|---|---|
| active substance (A) or (B) in basic form | 5 mg |
| acid/salt-forming agent in the amount needed to form a neutral salt | q.s. |
| glucose | 250 mg |
| human serum albumin | 10 mg |
| glycofurol | 250 mg |
| water for injections | ad 5 ml |

Method of Preparation

Dissolve the glycofurol and glucose in water for injections (WfI); add human serum albumin; add salt-forming agent; dissolve active substance with heating; make up to specified volume with WfI; transfer into ampoules under nitrogen gas.

EXAMPLE VII

Injectable Solution for Subcutaneous Administration Containing 5 mg of Active Substance (A) or (B) per 1 ml Composition:

| | |
|---|---|
| active substance (A) or (B) | 5 mg |
| glucose | 50 mg |
| polysorbate 80 (Tween 80) | 2 mg |
| water for injections | ad 1 ml |

Method of Preparation

Dissolve glucose and polysorbate in water for injections; dissolve active substance with heating or using ultrasound; make up to specified volume with WfI; transfer into ampoules under inert gas.

EXAMPLE VIII

Injectable Solution Containing 100 mg of Active Substance (A) or (B) per 10 ml

Composition:

| | |
|---|---|
| active substance (A) or (B) | 100 mg |
| monopotassium dihydrogen phosphate ($KH_2PO_4$) | 12 mg |
| disodium hydrogen phosphate ($Na_2HPO_4 \cdot 2H_2O$) | 2 mg |
| sodium chloride | 180 mg |
| human serum albumin | 50 mg |
| polysorbate 80 | 20 mg |
| water for injections | ad 10 ml |

Method of Preparation

Dissolve polysorbate 80, sodium chloride, monopotassium dihydrogen phosphate, and disodium hydrogen phosphate in water for injections (WfI); add human serum albumin; dissolve active substance with heating; make up to specified volume with WfI; transfer into ampoules.

EXAMPLE IX

Lyophilisate Containing 10 mg of Active Substance (A) or (B)

Composition:

| | |
|---|---|
| active substance (A) or (B) in basic form | 10 mg |
| acid/salt-forming agent in the amount needed to form a neutral salt | q.s. |
| mannitol | 300 mg |
| water for injections | ad 2 ml |

Method of Preparation

Dissolve mannitol in water for injections (WfI); add salt-forming agent; dissolve active substance with heating; make up to specified volume with WfI; transfer into vials; freeze-dry.

Solvent for Lyophilisate

| polysorbate 80 (Tween 80) | 20 mg |
|---|---|
| mannitol | 200 mg |
| water for injections | ad 10 ml |

Method of Preparation

Dissolve polysorbate 80 and mannitol in water for injections (WfI); transfer into ampoules.

EXAMPLE X

Lyophilisate Containing 5 mg of Active Substance (A) or (B)

Composition:

| active substance (A) or (B) in basic form | 5 mg |
|---|---|
| polar or nonpolar solvent (which can be removed by freeze drying) | ad 1 ml |

Method of Preparation

Dissolve active substance in suitable solvent; transfer into vials; freeze-dry.

Solvent for Lyophilisate

| polysorbate 80 (Tween 80) | 5 mg |
|---|---|
| mannitol | 100 mg |
| water for injections | ad 2 ml |

Method of Preparation

Dissolve polysorbate 80 and mannitol in water for injections (WfI); transfer into ampoules.

EXAMPLE XI

Tablets Containing 20 mg of Active Substance (A) or (B)

Composition:

| active substance (A) or (B) | 20 mg |
|---|---|
| lactose | 120 mg |
| maize starch | 40 mg |
| magnesium stearate | 2 mg |
| Povidone K 25 | 18 mg |

Method of Preparation

Homogeneously mix the active substance, lactose and maize starch; granulate with an aqueous solution of Povidone; mix with magnesium stearate; press in a tablet press; weight of tablet 200 mg.

EXAMPLE XII

Capsules Containing 20 mg of Active Substance (A) or (B)

Composition:

| active substance (A) or (B) | 20 mg |
|---|---|
| maize starch | 80 mg |
| highly dispersed silica | 5 mg |
| magnesium stearate | 2.5 mg |

Method of Preparation

Homogeneously mix the active substance, maize starch and silica; mix with magnesium stearate; transfer mixture into size 3 hard gelatine capsules in a capsule filling machine.

EXAMPLE XIII

Suppositories Containing 50 mg of Active Substance (A) or (B)

Composition:

| active substance (A) or (B) | 50 mg |
|---|---|
| hard fat (Adeps solidus) | q.s. ad 1700 mg |

Method of Preparation

Melt the hard fat at about 38° C.; homogeneously disperse the ground active substance in the molten hard fat; after cooling to about 35° C., pour into chilled molds.

EXAMPLE XIV

Aqueous Solution for Nasal Administration Containing 10 mg of Active Substance (A) or (B)

Composition:

| active substance (A) or (B) | 10.0 mg |
|---|---|
| hydrochloric acid in the amount needed to form a neutral salt | |
| methyl parahydroxybenzoate (PHB) | 0.01 mg |
| propyl parahydroxybenzoate (PHB) | 0.005 mg |
| purified water | ad 1.0 ml |

Method of Preparation

The active substance is dissolved in purified water; hydrochloric acid is added until the solution is clear; methyl and propyl PHB are added; the solution is made up to the specified volume with purified water; the solution is filtered sterile and transferred into a suitable container.

EXAMPLE XV

Aqueous Solution for Nasal Administration Containing 5 mg of Active Substance (A) or (B)

Composition:

| | |
|---|---|
| active substance (A) or (B) | 5 mg |
| 1,2-propanediol | 300 mg |
| hydroxyethylcellulose | 5 mg |
| sorbic acid | 1 mg |
| purified water | ad 1 ml |

Method of Preparation

The active substance is dissolved in 1,2-propanediol; a hydroxyethyl-cellulose solution in purified water containing sorbic acid is prepared and added to the solution of active substance; the solution is filtered sterile and transferred into a suitable container.

EXAMPLE XVI

Aqueous Solution for Intravenous Administration Containing 5 mg of Active Substance (A or (B)

Composition:

| | |
|---|---|
| active substance (A) or (B) | 5 mg |
| 1,2-propanediol | 300 mg |
| mannitol | 50 mg |
| water for injections (WfI) | ad 1 ml |

Method of Preparation

The active substance is dissolved in 1,2-propanediol; the solution is made up to approximately the specified volume with WfI; the mannitol is added and made up to approximately the specified volume with WfI; the solution is filtered sterile, transferred into individual containers and autoclaved.

EXAMPLE XVII

Liposomal Formulation for Intravenous Injection Containing 7.5 . mg of Active Substance (A) or (B)

Composition:

| | |
|---|---|
| active substance (A) or (B) | 7.5 mg |
| egg lecithin, e.g., Lipoid E 80 | 100.0 mg |
| cholesterol | 50.0 mg |
| glycerol | 50.0 mg |
| water for injections | ad 1.0 ml |

Method of Preparation

The active substance is dissolved in a mixture of lecithin and cholesterol; the solution is added to a mixture of glycerol and WfI and homogenized by high pressure homogenization or by the Microfluidizer technique; the liposomal formulation obtained is transferred into a suitable container under aseptic conditions.

EXAMPLE XVIII

Suspension for Nasal Administration Containing 20 mg of Active Substance (A) or (B)

Composition:

| | |
|---|---|
| active substance (A) or (B) | 20.0 mg |
| carboxymethylcellulose (CMC) | 20.0 mg |
| sodium monohydrogen phosphate/sodium dihydrogen phosphate buffer pH 6.8 | q.s. |
| sodium chloride | 8.0 mg |
| methyl parahydroxybenzoate | 0.01 mg |
| propyl parahydroxybenzoate | 0.003 mg |
| purified water | ad 1.0 ml |

Method of Preparation

The active substance is suspended in an aqueous CMC solution; the other ingredients are added successively to the suspension and the suspension is topped up to the specified volume with purified water.

EXAMPLE XIX

Aqueous Solution for Subcutaneous Administration with 10 mg of Active Substance (A) or (B)

Composition:

| | |
|---|---|
| active substance (A) or (B) | 10.0 mg |
| sodium monohydrogen phosphate/sodium dihydrogen phosphate buffer | q.s. ad pH 7.0 |
| sodium chloride | 4.0 mg |
| water for injections | ad 0.5 ml |

Method of Preparation

The active substance is dissolved in the phosphate buffer solution, after the addition of the common salt the solution is made up to the specified volume with water. The solution is filtered sterile, transferred into a suitable container and autoclaved.

EXAMPLE XX

Aqueous Suspension for Subcutaneous Administration Containing 5 mg of Active Substance (A) or (B)

Composition:

| | |
|---|---|
| active substance (A) or (B) | 5.0 mg |
| polysorbate 80 | 0.5 mg |
| water for injections | 0.5 ml |

Method of Preparation

The active substance is suspended in the polysorbate 80 solution and comminuted to a particle size of about 1 $\mu$m using a suitable dispersing technique (e.g., wet grinding, high pressure homogenization, microfluidization, etc.). The suspension is transferred into a corresponding container under aseptic conditions.

We claim:

1. A method for treating menopausal hot flushes, comprising administering to a host in need of such treatment an active substance selected from the group consisting of CGRP antagonists and CGRP release inhibitors.

2. The method according to claim 1, wherein the method is effected as a monotherapy with a single active substance.

3. The method according to claim 1, wherein the method is effected as a supplement to hormone replacement therapy.

4. The method according to claim 1, wherein the active substance is a CGRP antagonist.

5. The method according to claim 4, wherein the CGRP antagonist is selected from the group consisting of:

(A) 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine;

(B) 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine;

(C) 1-[$N^2$-[4-amino-3,5-dibromo-N-[[4-(3,4-dihydro-2(1H)-oxoquinazolin-3-yl)-1-piperidinyl]carbonyl]-D-phenylalanyl]-L-lysyl]-4-(4-pyridinyl)-piperazine;

(D) 1-[$N^2$-[4-amino-3,5-dibromo-N-[[4-(3,4-dihydro-2(1H)-oxoquinazolin-3-yl)-1-piperidinyl]carbonyl]-D-phenylalanyl]-L-lysyl]-4-(4-pyridinyl)-piperidine;

(E) 1-[$N^2$-[3,5-dibromo-N-[[4-(1,3-dihydro-4-phenyl-2(2H)-oxoimidazol-1-yl)-1-piperidinyl]carbonyl]-D-tyrosyl]-L-lysyl]-4-(4-pyridinyl)-piperazine;

(F) 1-[$N^2$-[4-amino-3,5-dibromo-N-[[4-(1,3-dihydro-4-phenyl-2(2H)-oxoimidazol-1-yl-1-piperidinyl]carbonyl]-D-phenyl-alanyl]-L-lysyl]-4-(4-pyridinyl)-piperazine;

(G) 1-[3,5-dibromo-N-[[4-(3,4-dihydro-2(1H)-oxothieno[3,4-d]pyrimidin-3-yl)-1-piperidinyl]carbonyl]-D-tyrosyl]-4-(1-piperidinyl)-piperidine;

(H) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-methyl-4-piperidinyl)-piperidine;

(I) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-piperidinyl)-piperidine;

(J) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-methyl-4-piperidinyl)-piperazine;

(K) 1-[4-amino-3,5-dibromo-N-[[4-(3,4-dihydro-2(1H)-oxothieno[3,2-d]pyrimidin-3-yl)-1-piperidinyl]carbonyl]-D-phenylalanyl]-4-(1-piperidinyl)-piperidine;

(L) 1-[4-amino-3,5-dibromo-N-[[4-[1,3-dihydro-4-[3-(tri-fluoromethyl)phenyl]-2(2H)-oxoimidazol-1-yl]-1-piperidinyl]carbonyl]-D-phenylalanyl]-4-(1-ethyl-4-piperidinyl)-piperidine;

(M) 1-[4-amino-3,5-dibromo-N-[[4-[3,4-dihydro-2(1H)-oxoquinazolin-3-yl]-1-piperidinyl]carbonyl]-D-phenylalanyl]-4-(1-hexyl-4-piperidinyl)-piperidine;

(N) 1-[4-amino-3,5-dibromo-N-[[4-[3,4-dihydro-2(1H)-oxoquinazolin-3-yl]-1-piperidinyl]carbonyl]-D-phenylalanyl]-4-(1-cyclopropylmethyl-4-piperidinyl)-piperidine;

(O) 1-[N-[[4-[3,4-dihydro-2(1H)-oxoquinazolin-3-yl]-1-piperidinyl]carbonyl]-3-ethenyl-D,L-phenylalanyl]-4-(hexahydro-1H-1-azepinyl)-piperidine;

(P) (R,S)-1-[4-[4-(3,4-dihydro-2(1H)-oxoquinazolin-3-yl)-1-piperidinyl]-2-[(4-hydroxy-3,5-dimethylphenyl)methyl]-1,4-dioxobutyl]-4-(1-piperidinyl)-piperidine;

(Q) 1-[4-amino-3,5-dibromo-N-[[4-[N-(aminocarbonyl)-N-phenylamino]-1-piperidinyl]carbonyl]-D-phenylalanyl]-4-(1-piperidinyl)-piperidine;

(R) 1-[4-amino-3,5-dibromo-N-[[4-(3,4-dihydro-2(1H)-oxoquinazolin-3-yl)-1-piperidinyl]carbonyl]-D-phenylalanyl]-4-(5-methoxy-4-pyrimidinyl)-piperazine;

(S) 1-[4-amino-3,5-dibromo-N-[[4-(1,1-dioxido-3(4H)-oxo-1,2,4-benzothiadiazin-2-yl)-1-piperidinyl]carbonyl]-D-phenylalanyl]-4-(1-piperidinyl)-piperidine;

(T) 1-[4-amino-3,5-dibromo-N-[[4-[2(1H)-oxoquinolin-3-yl]-1-piperidinyl]carbonyl]-D-phenylalanyl]-4-(1-piperidinyl)-piperidine;

(U) 1-[4-amino-3,5-dibromo-N-[[4-[3,4-dihydro-2(1H)-oxoquinazolin-3-yl]1-piperidinyl]carbonyl]-D-phenylalanyl]-4-[3-(dimethylamino)propyl]-piperazine;

(V) 1-[4-amino-3,5-dibromo-N-[[4-[3,4-dihydro-2(1H)-oxoquinazolin-3-yl]-1-piperidinyl]carbonyl]-D-phenylalanyl]-4-(4-methyl-1-piperazinyl)-piperidine;

(W) 1-[4-amino-3,5-dibromo-N-[[4-[3,4-dihydro-2(1H)-oxoquinazolin-3-yl]-1-piperidinyl]carbonyl]-D-phenylalanyl]-4-[(1-methyl-4-piperidinyl)carbonyl]-piperazine;

(X) 1-[4-amino-3,5-dibromo-N-[[4-[3,4-dihydro-2(1H)-oxoquinazolin-3-yl]-1-piperidinyl]carbonyl]-D-phenylalanyl]-4-[(1-methyl-4-piperazinyl)carbonyl]-piperazine;

(Y) 1-[4-amino-3,5-dibromo-N-[[4-(3,4-dihydro-2(1H)-oxoquinazolin-3-yl)-1-piperidinyl]carbonyl]-D-phenylalanyl]-4-[4-[4-(dimethylamino)butyl]phenyl]-piperazine;

(Z) 1-[4-amino-3,5-dibromo-N-[[4-(3,4-dihydro-2(1H)-oxoquinazolin-3-yl)-1-piperidinyl]carbonyl]-D-phenylalanyl]-4-[4-(dimethylamino)-1-piperidinyl]-piperidine;

(AA) 1-[$N^2$-[[4-(1,3-dihydro-4-phenyl-2(2H)-oxoimidazol-1-yl)-1-piperidinyl]carbonyl]-N'-methyl-D-tryptyl]-4-(4-methyl-1-piperazinyl)-piperidine;

(AB) 1-[$N^2$-[[4-(1,3-dihydro-4-phenyl-2(2H)-oxoimidazol-1-yl)-1-piperidinyl]carbonyl]-N'-(1,1-dimethylethoxycarbonyl)-D-tryptyl]-4-(1-methyl-4-piperidinyl)-piperidine;

(AC) (R,S)-1-[4-[4-(3,4-dihydro-2(1H)-oxoquinazolin-3-yl)-1-piperidinyl]-2-[(3,5-dibromo-4-methylphenyl)methyl]-1,4-dioxobutyl]-4-(4-methyl-1-piperazinyl)-piperidine;

(AD) (R,S)-1-[4-[4-(3,4-dihydro-2(1H)-oxoquinazolin-3-yl)-1-piperidinyl]-2-[(3,5-dibromo-4-methoxyphenyl)methyl]-1,4-dioxobutyl]-4-(1-methyl-4-piperidinyl)-piperidine;

(AE) (R,S)-1-[4-[4-(3,4-dihydro-2(1H)-oxoquinazolin-3-yl)-1-piperidinyl]-2-[(3,4-dibromophenyl)methyl]-1,4-dioxobutyl]-4-(4-methyl-1-piperazinyl)-piperidine;

(AF) 1-[N -[N-[[4-(1,3-dihydro-2(2H)-oxobenzimidazol-1-yl)-1-piperidinyl]carbonyl]-3,5-dibromo-D-tyrosyl]-L-lysyl]-4-(4-pyridinyl)-piperazine;

(AG) 1-[4-amino-3,5-dibromo-N-[[4-(1,3-dihydro-6-hydroxy-2(2H)-oxobenzimidazol-1-yl)-1-piperidinyl]carbonyl]-D-phenylalanyl]-4-(1-piperidinyl)-piperidine;

(AH) 1-[$N^2$-[4-amino-3,5-dibromo-N-[[4-(1,3-dihydro-2(2H)-oxobenzimidazol-1-yl)-1-piperidinyl]carbonyl]-

D-phenylalanyl]-N$^6$,N$^6$-dimethyl-L-lysyl]-4-(4-pyridinyl)-piperazine;

(AI) 1-[N$^2$-[4-amino-3,5-dibromo-N-[[4-(3,4-dihydro-2 (1H)-oxoquinazolin-3-yl)-1-piperidinyl]carbonyl]-D-phenylalanyl]-N$^6$,N$^6$-dimethyl-L-lysyl]-4-(4-pyridinyl)-piperazine;

(AJ) (R,S)-1-[2-(4-amino-3,5-dibromobenzoyl)-4-[4-(3, 4-dihydro-2(1H)-oxoquinazolin-3-yl)-1-piperidinyl]-4-oxobutyl]-4-(-piperidinyl)-piperidine;

(AK) 1-[4-amino-3,5-dibromo-N-[[4-(3,4-dihydro-2,2-dioxido-2,1,3-benzothiadiazin-3-yl)-1-piperidinyl] carbonyl]-D-phenylalanyl]-4-(1-piperidinyl)-piperidine;

(AL) 1-[4-amino-3,5-dibromo-N-[[4-[1,3-dihydro-2(2H)-oxoimidazo[4,5-c]quinolin-3-yl]-1-piperidinyl] carbonyl]-D-phenyl-alanyl]-4-(1-piperidinyl) carbonyl]-piperidine;

(AM) 1-[4-amino-3,5-dibromo-N-[[4-(3,4-dihydro-2 (1H)-oxoquinazolin-3-yl)-1-piperidinyl]carbonyl]-D-phenylalanyl]-4-(1-piperidinyl)-piperidine;

(AN) 1-[N$^2$-[3,5-dibromo-N-[[4-(3,4-dihydro-2(1H)-oxoquinazolin-3-yl)-1-piperidinyl]carbonyl]-D-tyrosyl]-N$^6$,N$^6$-dimethyl-L-lysyl]-4-(4-pyridinyl)-piperazine ;

(AO) 1-[4-amino-N-[[4-[4-(3-bromophenyl)-1,3-dihydro-2(2H)-oxoimidazol-1-yl]-1-piperidinyl] carbonyl]-3,5-dibromo-D-phenylalanyl]-4-(1-methyl-4-piperidinyl)-piperidine;

(AP) 1-[4-amino-3,5-dibromo-N-[[4-[1,3-dihydro-4-phenyl-2(2H)-oxoimidazol-1-yl]-piperidinyl] carbonyl]-D-phenylalanyl]-4-(4-methyl-1-piperazinyl)-piperidine;

(AQ) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-piperidinyl)-piperidine;

(AR) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(exo-8-methyl-8-azabicyclo[3,2,1]oct-3-yl)-piperazine;

(AS) 1-[3,5-dibromo-N-[[4-(1,3-dihydro-4-phenyl-2 (2H)-oxoimidazol-1-yl)-1-piperidinyl]carbonyl]-D-tyrosyl]-4-(1-piperidinyl)-piperidine;

(AT) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-ethyl-4-piperidinyl)-piperazine;

(AU) 1-[4-amino-3,5-dibromo-N-[[4-[1,3-dihydro-4-phenyl-2(2H)-oxoimidazol-1-yl]-1-piperidinyl] carbonyl]-D-phenylalanyl]-4-(hexahydro-4-methyl-1H-1,4-diazepin-1-yl)piperidine;

(AV) 1-[3,5-dibromo-N-[[4-(3,4-dihydro-2(1H)-oxoquinazolin-3-yl)-1-piperidinyl]carbonyl]-D-tyrosyl]-4-[1-(methylsulfonyl)-4-piperidinyl]-piperidine;

(AW) 1-[4-amino-3,5-dibromo-N-[[4-(1,3-dihydro-4-phenyl-2(2H)-oxoimidazol-1-yl)-1-piperidinyl] carbonyl]-D-phenylalanyl]-4-(1-methyl-4-piperidinyl)-piperidine;

(AX) 1-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(hexahydro-1H-1-azepinyl)-piperidine;

(AY) 1-[3,5-dibromo-N-[[4-(3,4-dihydro-2(1H)-oxoquinazolin-3-yl)-1-piperidinyl]carbonyl]-D-tyrosyl]-4-(1-methyl-4-piperidinyl)-piperidine;

(AZ) 1-[4-amino-3,5-dibromo-N-[[4-(3,4-dihydro-2(1H)-oxoquinazolin-3-yl)-1-piperidinyl]carbonyl]-D-phenylalanyl]-4-(exo-8-methyl-8-azabicyclo[3,2,1] oct-3-yl)-piperazine;

(BA) 1-[4-amino-3,5-dibromo-N-[[4-(1,3-dihydro-4-phenyl-2(2H)-oxoimidazol-1-yl)-1-piperidinyl] carbonyl]-D-phenylalanyl]-4-(1-methyl-4-piperidinyl)-piperazine;

(BB) 1-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(1-piperidinyl)-piperidine;

(BC) 1-[N$^6$-Acetyl-N$^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine;

(BD) 1-[3,5-dibromo-N-[[4-(1,3-dihydro-4-phenyl-2 (2H)-oxoimidazol-1-yl)-1-piperidinyl]carbonyl]-D-tyrosyl]-4-(hexahydro-1H-1-azepinyl)-piperidine;

(BE) 1-[4-amino-3,5-dibromo-N-[[4-(1,3-dihydro-4-(3-thienyl)-2(2H)-oxoimidazol-1-yl]-1-piperidinyl] carbonyl]-D-phenyl-alanyl]-4-(1-methyl-4-piperidinyl)-piperidine;

(BF) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-methyl-4-piperidinyl)-piperidine;

(BG) 1-[3,5-dibromo-N-[[4-(3,4-dihydro-2(1H)-oxoquinazolin-3-yl)-1-piperidinyl]carbonyl]-D-tyrosyl]-4-[1-(hydroxycarbonylmethyl)-4-piperidinyl]-piperidine;

(BH) 1-[4-amino-3,5-dibromo-N-[[4-[3,4-dihydro-2 (1H)-oxoquinazolin-3-yl]-1-piperidinyl]carbonyl]-D-phenylalanyl]-4-(1-methylsulphonyl-4-piperidinyl)-piperidine;

(BI) 1-[3,5-dibromo-N-[[4-(3,4-dihydro-2(1H)-oxoquinazolin-3-yl)-1-piperidinyl]carbonyl]-D-tyrosyl]-4-(4-piperidinyl)-piperidine;

(BJ) 1-[4-amino-3,5-dibromo-N-[[4-(1,3-dihydro-4-phenyl-2(2H)-oxoimidazol-1-yl)-1-piperidinyl] carbonyl]-D-phenylalanyl]-4-(1-ethyl-4-piperidinyl)-piperidine;

(BK) 1-[4-amino-3,5-dibromo-N-[[4-(1,3-dihydro-4-(3-hydroxyphenyl)-2(2H)-oxoimidazol-1-yl)-1-piperidinyl]carbonyl]-D-phenylalanyl]-4-(1-methyl-4-piperidinyl)-piperidine;

(BL) 1-[3,5-dibromo-N-[[4-(3,4-dihydro-2(1H)-oxoquinazolin-3-yl)-1-piperidinyl]carbonyl]-D-tyrosyl]-4-(hexahydro-1H-1-azepinyl)-piperidine;

(BM) 1-[4-amino-3,5-dibromo-N-[[4-(1,3-dihydro-4-phenyl-2(2H)-oxoimidazol-1-yl)-1-piperidinyl] carbonyl]-D-phenylalanyl]-4-(1-piperidinyl)-piperidine;

(BN) 1-[4-amino-3,5-dibromo-N-[[4-[4-(3-bromophenyl)-1,3-dihydro-2(2H)-oxoimidazol-1-yl]-1-piperidinyl]carbonyl]-D-phenylalanyl]-4-(exo-8-methyl-8-azabicyclo[3,2,1]oct-3-yl)-piperazine;

(BO) 1-[4-amino-3,5-dibromo-N-[[4-(3,4-dihydro-2 (1H)-oxoquinazolin-3-yl)-1-piperidinyl]carbonyl]-D-phenylalanyl]-4-(1-ethyl-4-piperidinyl)-piperidine;

(BP) 1-[4-amino-3,5-dibromo-N-[[4-(3,4-dihydro-2(1H)-oxoquinazolin-3-yl)-1-piperidinyl]carbonyl]-D-phenylalanyl]-4-(1-ethyl-4-piperidinyl)-piperazine;

(BQ) 1-[4-amino-3,5-dibromo-N-[[4-[1,3-dihydro-4-(3-methoxyphenyl)-2(2H)-oxoimidazol-1-yl]-1- piperidinyl]carbonyl]-D-phenylalanyl]-4-(exo-8-methyl-8-azabicyclo[3,2,1]oct-3-yl)-piperazine;

(BR) 1-[3,5-dibromo-N-[[4-(3,4-dihydro-2(1H)-oxoquinazolin-3-yl)-1-piperidinyl]carbonyl]-D-tyrosyl]-4-[1-(cyclopropyl-methyl)-4-piperidinyl]-piperidine;

(BS) 1-[4-amino-3,5-dibromo-N-[[4-(3,4-dihydro-2(1H)-oxoquinazolin-3-yl)-1-piperidinyl]carbonyl]-D-phenylalanyl]-4-(hexahydro-1H-1-azepinyl)-piperidine;

(BT) 1-[4-amino-3,5-dibromo-N-[[4-(3,4-dihydro-2(1H)-oxoquinazolin-3-yl)-1-piperidinyl]carbonyl]-D-phenylalanyl]-4-(4-piperidinyl)-piperidine;

(BU) 1-[3,5-dibromo-N-[[4-(1,3-dihydro-4-phenyl-2(2H)-oxoimidazol-1-yl)-1-piperidinyl]carbonyl]-D-tyrosyl]-4-(4-pyridinyl)-piperidine;

(BV) 1-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(-methyl-4-piperidinyl)-piperazine;

(BW) 1-[$N^2$-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-L-lysyl]-4-(4-pyridinyl)-piperazine;

(BX) 1-[3,5-dibromo-N-[[4-(1,3-dihydro-4-(3-thienyl)-2(2H)-oxoimidazol-1-yl)-1-piperidinyl]carbonyl]-D-tyrosyl]-4-(1-piperidinyl)-piperidine;

(BY) 1-[4-amino-N-[[4-[4-(3-chlorophenyl)-1,3-dihydro-2(2H)-oxoimidazol-1-yl]-1-piperidinyl]carbonyl]-3,5-dibromo-D-phenylalanyl]-4-(1-methyl-4-piperidinyl)-piperidine;

(BZ) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(hexahydro-1H-1-azepinyl)-piperidine;

(CA) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-methyl-4-piperidinyl)-piperazine;

(CB) 1-[4-amino-N-[[4-[4-(3-chlorophenyl)-1,3-dihydro-2(2H)-oxoimidazol-1-yl]-1-piperidinyl]carbonyl]-3,5-dibromo-D-phenylalanyl]-4-(hexahydro-1H-1-azepinyl)-piperidine;

(CC) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(4-pyridinyl)-piperazine;

(CD) 1-[3,5-dibromo-N-[[4-(1,3-dihydro-4-phenyl-2(2H)-oxoimidazol-1-yl)-1-piperidinyl]carbonyl]-D-tyrosyl]-4-(1-methyl-4-piperidinyl)-piperidine;

(CE) 1-[4-amino-3,5-dibromo-N-[[4-[1,3-dihydro-4-phenyl-2(2H)-oxoimidazol-1-yl]-1-piperidinyl]carbonyl]-D-phenylalanyl]-4-[4-(1-oxoethyl)phenyl]-piperazine;

(CF) 1-[3,5-dibromo-N-[[4-[3,4-dihydro-2(1H)-oxoquinazolin-3-yl]-1-piperidinyl]carbonyl]-D-tyrosyl]-4-(1-methyl-4-piperidinyl)-piperazine;

(CG) 1-[4-amino-3,5-dibromo-N-[[4-[1,3-dihydro-4-(3-nitrophenyl)-2(2H)-oxoimidazol-1-yl]-1-piperidinyl]carbonyl]-D-phenylalanyl]-4-(-methyl-4-piperidinyl)-piperidine;

(CH) 1-[4-amino-3,5-dibromo-N-[[4-[3,4-dihydro-2(1H)-oxoquinazolin-3-yl]-1-piperidinyl]carbonyl]-D-phenylalanyl]-4-(1-pyrrolidinyl)-piperidine;

(CI) 1-[4-amino-3,5-dibromo-N-[[4-(1,3-dihydro-4-phenyl-2(2H)-oxoimidazol-1-yl]-1-piperidinyl] carbonyl]-D-phenylalanyl]-4-(hexahydro-1H-1-azepinyl)-piperidine; and (CJ) 1-[4-amino-3,5-dibromo-N-[[4-(1,3-dihydro-4-(3-thienyl)-2(2H)-oxoimidazol-1-yl)-1-piperidinyl]carbonyl]-D-phenyl-alanyl]-4-(1-methyl-4-piperidinyl)-piperazine, the tautomers, the diastereomers, the enantiomers, the mixtures thereof and the physiologically acceptable salts thereof.

6. A pharmaceutical composition for treating menopausal hot flushes comprising an active substance selected from CGRP antagonists and CGRP release inhibitors.

7. The pharmaceutical composition according to claim 6, wherein the pharmaceutical composition contains only one active substance.

8. The pharmaceutical composition according to claim 6, wherein the active substance is a CGRP antagonist.

9. The pharmaceutical composition according to claim 8, wherein the CGRP antagonist is selected from the group consisting of:

(A) 1-[$N^2$-[3,5-dibromo-N-[[4-(3,4-dihydro-2(1H)-oxoquinazolin-3-yl) 1-piperidinyl]carbonyl]-D-tyrosyl]-L-lysyl]-4-(4-pyridinyl)-piperazine;

(B) 1-[4-amino-3,5-dibromo-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidine;

(C) 1-[$N^2$-[4-amino-3,5-dibromo-N-[[4-(3,4-dihydro-2(1H)-oxoquinazolin-3-yl)-1-piperidinyl]carbonyl]-D-phenylalanyl]-L-lysyl]-4-(4-pyridinyl)-piperazine;

(D) 1-[$N^2$-[4-amino-3,5-dibromo-N-[[4-(3,4-dihydro-2(1H)-oxoquinazolin-3-yl)-1-piperidinyl]carbonyl]-D-phenylalanyl]-L-lysyl]-4-(4-pyridinyl)-piperidine;

(E) 1-[$N^2$-[3,5-dibromo-N-[[4-(1,3-dihydro-4-phenyl-2(2H)-oxoimidazol-1-yl)-1-piperidinyl]carbonyl]-D-tyrosyl]-L-lysyl]-4-(4-pyridinyl)-piperazine;

(F) 1-[$N^2$-[4-amino-3,5-dibromo-N-[[4-(1,3-dihydro-4-phenyl-2(2H)-oxoimidazol-1-yl)-1-piperidinyl]carbonyl]-D-phenyl-alanyl]-L-lysyl]-4-(4-pyridinyl)-piperazine;

(G) 1-[3,5-dibromo-N-[[4-(3,4-dihydro-2(1H)-oxothieno[3,4-d]pyrimidin-3-yl)-1-piperidinyl]carbonyl]-D-tyrosyl]-4-(1-piperidinyl)-piperidine;

(H) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-methyl-4-piperidinyl)-piperidine;

(I) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-piperidinyl)-piperidine;

(J) 1-[4-amino-3,5-dibromo-N-[[4-(2,4-dihydro-5-phenyl-3(3H)-oxo-1,2,4-triazol-2-yl)-1-piperidinyl]carbonyl]-D-phenyl-alanyl]-4-(1-methyl-4-piperidinyl)-piperazine;

(K) 1-[4-amino-3,5-dibromo-N-[[4-(3,4-dihydro-2(1H)-oxothieno[3,2-d]pyrimidin-3-yl)-1-piperidinyl]carbonyl]-D-phenyl-alanyl]-4-(1-piperidinyl)-piperidine;

(L) 1-[4-amino-3,5-dibromo-N-[[4-[1,3-dihydro-4-[3-(tri-fluoromethyl)phenyl]-2(2H)-oxoimidazol-1-yl]-1-piperidinyl]carbonyl]-D-phenylalanyl]-4-(1-ethyl-4-piperidinyl)-piperidine;

(M) 1-[4-amino-3,5-dibromo-N-[[4-[3,4-dihydro-2(1H)-oxoquinazolin-3-yl]-1-piperidinyl]carbonyl]-D-phenylalanyl]-4-(1-hexyl-4-piperidinyl)-piperidine;

(N) 1-[4-amino-3,5-dibromo-N-[[4-[3,4-dihydro-2(1H)-oxoquinazolin-3-yl]-1-piperidinyl]carbonyl]-D-phenylalanyl]-4-(1-cyclopropylmethyl-4-piperidinyl)-piperidine;

(O) 1-[N-[[4-[3,4-dihydro-2(1H)-oxoquinazolin-3-yl]-1-piperidinyl]carbonyl]-3-ethenyl-D,L-phenylalanyl]-4-(hexahydro-1H-1-azepinyl)-piperidine;

(P) (R,S)-1-[4-[4-(3,4-dihydro-2(1H)-oxoquinazolin-3-yl)-1-piperidinyl]-2-[(4-hydroxy-3,5-dimethylphenyl)methyl]-1,4-dioxobutyl]-4-(1-piperidinyl)-piperidine;

(Q) 1-[4-amino-3,5-dibromo-N-[[4-[N-(aminocarbonyl)-N-phenylamino]-1-piperidinyl]carbonyl]-D-phenylalanyl]-4-(1-piperidinyl)-piperidine;

(R) 1-[4-amino-3,5-dibromo-N-[[4-(3,4-dihydro-2(1H)-oxoquinazolin-3-yl)-1-piperidinyl]carbonyl]-D-phenylalanyl]-4-(5-methoxy-4-pyrimidinyl)-piperazine;

(S) 1-[4-amino-3,5-dibromo-N-[[4-(1,1-dioxido-3(4H)-oxo-1,2,4-benzothiadiazin-2-yl)-1-piperidinyl]carbonyl]-D-phenylalanyl]-4-(1-piperidinyl)-piperidine;

(T) 1-[4-amino-3,5-dibromo-N-[[4-[2(1H)-oxoquinolin-3-yl]-1-piperidinyl]carbonyl]-D-phenylalanyl]-4-(1-piperidinyl)-piperidine;

(U) 1-[4-amino-3,5-dibromo-N-[[4-[3,4-dihydro-2(1H)-oxoquinazolin-3-yl]-1-piperidinyl]carbonyl]-D-phenylalanyl]-4-[3-(dimethylamino)propyl]-piperazine;

(V) 1-[4-amino-3,5-dibromo-N-[[4-[3,4-dihydro-2(1H)-oxoquinazolin-3-yl]-1-piperidinyl]carbonyl]-D-phenylalanyl]-4-(4-methyl-1-piperazinyl)-piperidine;

(W) 1-[4-amino-3,5-dibromo-N-[[4-[3,4-dihydro-2(1H)-oxoquinazolin-3-yl]-1-piperidinyl]carbonyl]-D-phenylalanyl]-4-[(1-methyl-4-piperidinyl)carbonyl]-piperazine;

(X) 1-[4-amino-3,5-dibromo-N-[[4-[3,4-dihydro-2(1H)-oxoquinazolin-3-yl]-1-piperidinyl]carbonyl]-D-phenylalanyl]-4-[(1-methyl-4-piperazinyl)carbonyl]-piperazine;

(Y) 1-[4-amino-3,5-dibromo-N-[[4-(3,4-dihydro-2(1H)-oxoquinazolin-3-yl)-1-piperidinyl]carbonyl]-D-phenylalanyl]-4-[4-[4-(dimethylamino)butyl]phenyl]-piperazine;

(Z) 1-[4-amino-3,5-dibromo-N-[[4-(3,4-dihydro-2(1H)-oxoquinazolin-3-yl)-1-piperidinyl]carbonyl]-D-phenylalanyl]-4-[4-(dimethylamino)-1-piperidinyl]-piperidine;

(AA) 1-[$N^2$-[[4-(1,3-dihydro-4-phenyl-2(2H)-oxoimidazol-1-yl)-1-piperidinyl]carbonyl]-N'-methyl-D-tryptyl]-4-(4-methyl-1-piperazinyl)-piperidine;

(AB) 1-[$N^2$-[[4-(1,3-dihydro-4-phenyl-2(2H)-oxoimidazol-1-yl)-1-piperidinyl]carbonyl]-N'-(1,1-dimethylethoxycarbonyl)-D-tryptyl]-4-(1-methyl-4-piperidinyl)-piperidine;

(AC) (R,S)-1-[4-[4-(3,4-dihydro-2(1H)-oxoquinazolin-3-yl)-1-piperidinyl]-2-[(3,5-dibromo-4-methylphenyl)methyl]-1,4-dioxobutyl]-4-(4-methyl-1-piperazinyl)-piperidine;

(AD) (R,S)-1-[4-[4-(3,4-dihydro-2(1H)-oxoquinazolin-3-yl)-1-piperidinyl]-2-[(3,5-dibromo-4-methoxyphenyl)methyl]-1,4-dioxobutyl]-4-(-methyl-4-piperidinyl)-piperidine;

(AE) (R,S)-1-[4-[4-(3,4-dihydro-2(1H)-oxoquinazolin-3-yl)-1-piperidinyl]-2-[(3,4-dibromophenyl)methyl]-1,4-dioxobutyl]-4-(4-methyl-1-piperazinyl)-piperidine;

(AF) 1-[$N^2$-[N-[[4-(1,3-dihydro-2(2H)-oxobenzimidazol-1-yl)-1-piperidinyl]carbonyl]-3,5-dibromo-D-tyrosyl]-L-lysyl]-4-(4-pyridinyl)-piperazine;

(AG) 1-[4-amino-3,5-dibromo-N-[[4-(1,3-dihydro-6-hydroxy-2(2H)-oxobenzimidazol-1-yl)-1-piperidinyl]carbonyl]-D-phenylalanyl]-4-(1-piperidinyl)-piperidine;

(AH) 1-[$N^2$-[4-amino-3,5-dibromo-N-[[4-(1,3-dihydro-2(2H)-oxobenzimidazol-1-yl)-1-piperidinyl]carbonyl]-D-phenylalanyl]-$N^6$,$N^6$-dimethyl-L-lysyl]-4-(4-pyridinyl)-piperazine;

(AI) 1-[$N^2$-[4-amino-3,5-dibromo-N-[[4-(3,4-dihydro-2(1H)-oxoquinazolin-3-yl)-1-piperidinyl]carbonyl]-D-phenylalanyl]-$N^6$,$N^6$-dimethyl-L-lysyl]-4-(4-pyridinyl)-piperazine;

(AJ) (R,S)-1-[2-(4-amino-3,5-dibromobenzoyl)-4-[4-(3,4-dihydro-2(1H)-oxoquinazolin-3-yl)-1-piperidinyl]-4-oxobutyl]-4-(1-piperidinyl)-piperidine;

(AK) 1-[4-amino-3,5-dibromo-N-[[4-(3,4-dihydro-2,2-dioxido-2,1,3-benzothiadiazin-3-yl)-1-piperidinyl]carbonyl]-D-phenylalanyl]-4-(1-piperidinyl)-piperidine;

(AL) 1-[4-amino-3,5-dibromo-N-[[4-[1,3-dihydro-2(2H)-oxoimidazo[4,5-c]quinolin-3yl]-1-piperidinyl]carbonyl]-D-phenyl-alanyl]-4-(1-piperidinyl)carbonyl]-piperidine;

(AM) 1-[4-amino-3,5-dibromo-N-[[4-(3,4-dihydro-2(1H)-oxoquinazolin-3-yl)-1-piperidinyl]carbonyl]-D-phenylalanyl]-4-(1-piperidinyl)-piperidine;

(AN) 1-[$N^2$-[3,5-dibromo-N-[[4-(3,4-dihydro-2(1H)-oxoquinazolin-3-yl)-1-piperidinyl]carbonyl]-D-tyrosyl]-$N^6$,$N^6$-dimethyl-L-lysyl]-4-(4-pyridinyl)-piperazine;

(AO) 1-[4-amino-N-[[4-[4-(3-bromophenyl)-1,3-dihydro-2(2H)-oxoimidazol-1-yl]-1-piperidinyl]carbonyl]-3,5-dibromo-D-phenylalanyl]-4-(1-methyl-4-piperidinyl)-piperidine;

(AP) 1-[4-amino-3,5-dibromo-N-[[4-[1,3-dihydro-4-phenyl-2(2H)-oxoimidazol-1-yl]-1-piperidinyl]carbonyl]-D-phenylalanyl]-4-(4-methyl-1-piperazinyl)-piperidine;

(AQ) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-piperidinyl)-piperidine;

(AR) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(exo-8-methyl-8-azabicyclo[3,2,1]oct-3-yl)-piperazine;

(AS) 1-[3,5-dibromo-N-[[4-(1,3-dihydro-4-phenyl-2(2H)-oxoimidazol-1-yl)-1-piperidinyl]carbonyl]-D-tyrosyl]-4-(1-piperidinyl)-piperidine;

(AT) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-ethyl-4-piperidinyl)-piperazine;

(AU) 1-[4-amino-3,5-dibromo-N-[[4-[1,3-dihydro-4-phenyl-2(2H)-oxoimidazol-1-yl]-1-piperidinyl]carbonyl]-D-phenylalanyl]-4-(hexahydro-4-methyl-1H-1,4-diazepin-1-yl)piperidine;

(AV) 1-[3,5-dibromo-N-[[4-(3,4-dihydro-2(1H)-oxoquinazolin-3-yl)-1-piperidinyl]carbonyl]-D-tyrosyl]-4-[1-(methylsulfonyl)-4-piperidinyl]-piperidine;

(AW) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(1-methyl-4-piperidinyl)-piperidine;

(AX) 1-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(hexahydro-1H-1-azepinyl)-piperidine;

(AY) 1-[3,5-dibromo-N-[[4-(3,4-dihydro-2(1H)-oxoquinazolin-3-yl)-1-piperidinyl]carbonyl]-D-tyrosyl]-4-(1-methyl-4-piperidinyl)-piperidine;

(AZ) 1-[4-amino-3,5-dibromo-N-[[4-(3,4-dihydro-2(1H)-oxoquinazolin-3-yl)-1-piperidinyl]carbonyl]-D-phenylalanyl]-4-(exo-8-methyl-8-azabicyclo[3,2,1]oct-3-yl)-piperazine;

(BA) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(1-methyl-4-piperidinyl)-piperazine;

(BB) 1-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(1-piperidinyl)-piperidine;

(BC) 1-[N$^6$-Acetyl-N$^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine;

(BD) 1-[3,5-dibromo-N-[[4-(1,3-dihydro-4-phenyl-2(2H)-oxoimidazol-1-yl)-1-piperidinyl]carbonyl]-D-tyrosyl]-4-(hexahydro-1H-1-azepinyl)-piperidine;

(BE) 1-[4-amino-3,5-dibromo-N-[[4-(1,3-dihydro-4-(3-thienyl)-2(2H)-oxoimidazol-1-yl)-1-piperidinyl]carbonyl]-D-phenyl-alanyl]-4-(1-methyl-4-piperidinyl)-piperidine;

(BF) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-methyl-4-piperidinyl)-piperidine;

(BG) 1-[3,5-dibromo-N-[[4-(3,4-dihydro-2(1H)-oxoquinazolin-3-yl)-1-piperidinyl]carbonyl]-D-tyrosyl]-4-[1-(hydroxycarbonylmethyl)-4-piperidinyl]-piperidine;

(BH) 1-[4-amino-3,5-dibromo-N-[[4-[3,4-dihydro-2(1H)-oxoquinazolin-3-yl]-1-piperidinyl]carbonyl]-D-phenylalanyl]-4-(1-methylsulphonyl-4-piperidinyl)-piperidine;

(BI) 1-[3,5-dibromo-N-[[4-(3,4-dihydro-2(1H)-oxoquinazolin-3-yl)-1-piperidinyl]carbonyl]-D-tyrosyl]-4-(4-piperidinyl)-piperidine;

(BJ) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(1-ethyl-4-piperidinyl)-piperidine;

(BK) 1-[4-amino-3,5-dibromo-N-[[4-(1,3-dihydro-4-(3-hydroxyphenyl)-2(2H)-oxoimidazol-1-yl)-1-piperidinyl]carbonyl]-D-phenylalanyl]-4-(1-methyl-4-piperidinyl)-piperidine;

(BL) 1-[3,5-dibromo-N-[[4-(3,4-dihydro-2(1H)-oxoquinazolin-3-yl)-1-piperidinyl]carbonyl]-D-tyrosyl]-4-(hexahydro-1H-1-azepinyl)-piperidine;

(BM) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(1-piperidinyl)-piperidine;

(BN) 1-[4-amino-3,5-dibromo-N-[[4-[4-(3-bromophenyl)-1,3-dihydro-2(2H)-oxoimidazol-1-yl]-1-piperidinyl]carbonyl]-D-phenylalanyl]-4-(exo-8-methyl-8-azabicyclo[3,2,1]oct-3-yl)-piperazine;

(BO) 1-[4-amino-3,5-dibromo-N-[[4-(3,4-dihydro-2(1H)-oxoquinazolin-3-yl)-1-piperidinyl]carbonyl]-D-phenylalanyl]-4-(1-ethyl-4-piperidinyl)-piperidine;

(BP) 1-[4-amino-3,5-dibromo-N-[[4-(3,4-dihydro-2(1H)-oxoquinazolin-3-yl)-1-piperidinyl]carbonyl]-D-phenylalanyl]-4-(1-ethyl-4-piperidinyl)-piperazine;

(BQ) 1-[4-amino-3,5-dibromo-N-[[4-[1,3-dihydro-4-(3-methoxyphenyl)-2(2H)-oxoimidazol-1-yl]-1-piperidinyl]carbonyl]-D-phenylalanyl]-4-(exo-8-methyl-8-azabicyclo[3,2,1]oct-3-yl)-piperazine;

(BR) 1-[3,5-dibromo-N-[[4-(3,4-dihydro-2(1H)-oxoquinazolin-3-yl)-1-piperidinyl]carbonyl]-D-tyrosyl]-4-[1-(cyclopropyl-methyl)-4-piperidinyl]-piperidine;

(BS) 1-[4-amino-3,5-dibromo-N-[[4-(3,4-dihydro-2(1H)-oxoquinazolin-3-yl)-1-piperidinyl]carbonyl]-D-phenylalanyl]-4-(hexahydro-1H-1-azepinyl)-piperidine;

(BT) 1-[4-amino-3,5-dibromo-N-[[4-(3,4-dihydro-2(1H)-oxoquinazolin-3-yl)-1-piperidinyl]carbonyl]-D-phenylalanyl]-4-(4-piperidinyl)-piperidine;

(BU) 1-[3,5-dibromo-N-[[4-(1,3-dihydro-4-phenyl-2(2H)-oxoimidazol-1-yl)-1-piperidinyl]carbonyl]-D-tyrosyl]-4-(4-pyridinyl)-piperidine;

(BV) 1-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-4-(1-methyl-4-piperidinyl)-piperazine;

(BW) 1-[N$^2$-[3,5-dibromo-N-[[4-[1,3-dihydro-4-[3-(trifluoromethyl)phenyl]-2(2H)-oxoimidazol-1-yl]-1-piperidinyl]carbonyl]-D-tyrosyl]-L-lysyl]-4-(4-pyridinyl)-piperazine;

(BX) 1-[3,5-dibromo-N-[[4-(1,3-dihydro-4-(3-thienyl)-2(2H)-oxoimidazol-1-yl)-1-piperidinyl]carbonyl]-D-tyrosyl]-4-(1-piperidinyl)-piperidine;

(BY) 1-[4-amino-N-[[4-[4-(3-chlorophenyl)-1,3-dihydro-2(2H)-oxoimidazol-1-yl]-1-piperidinyl]carbonyl]-3,5-dibromo-D-phenylalanyl]-4-(1-methyl-4-piperidinyl)-piperidine;

(BZ) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(hexahydro-1H-1-azepinyl)-piperidine;

(CA) 1-[4-amino-3,5-dibromo-N-[[4-[1,3-dihydro-4-[3-(trifluoromethyl)phenyl]-2(2H)-oxoimidazol-1-yl]-1-piperidinyl]carbonyl]-D-phenylalanyl]-4-(1-methyl-4-piperidinyl)-piperazine;

(CB) 1-[4-amino-N-[[4-[4-(3-chlorophenyl)-1,3-dihydro-2(2h)-oxoimidazol-1-yl]-1-piperidinyl]carbonyl]-3,5-dibromo-D-phenylalanyl]-4-(hexahydro-1H-1-azepinyl)-piperidine;

(CC) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(4-pyridinyl)-piperazine;

(CD) 1-[3,5-dibromo-N-[[4-(1,3-dihydro-4-phenyl-2(2H)-oxoimidazol-1-yl)-1-piperidinyl]carbonyl]-D-tyrosyl]-4-(1-methyl-4-piperidinyl)-piperidine;

(CE) 1-[4-amino-3,5-dibromo-N-[[4-[1,3-dihydro-4-phenyl-2(2H)-oxoimidazol-1-yl]-1-piperidinyl]carbonyl]-D-phenylalanyl]-4-[4-(1-oxoethyl)phenyl]-piperazine;

(CF) 1-[3,5-dibromo-N-[[4-[3,4-dihydro-2(1H)-oxoquinazolin-3-yl]-1-piperidinyl]carbonyl]-D-tyrosyl]-4-(1-methyl-4-piperidinyl)-piperazine;

(CG) 1-[4-amino-3,5-dibromo-N-[[4-[1,3-dihydro-4-(3-nitrophenyl)-2(2H)-oxoimidazol-1-yl]-1-piperidinyl]carbonyl]-D-phenylalanyl]-4-(1-methyl-4-piperidinyl)-piperidine;

(CH) 1-[4-amino-3,5-dibromo-N-[[4-[3,4-dihydro-2(1H)-oxoquinazolin-3-yl]-1-piperidinyl]carbonyl]-D-phenylalanyl]-4-(1-pyrrolidinyl)-piperidine;

(CI) 1-[4-amino-3,5-dibromo-N-[[4-(1,3-dihydro-4-phenyl-2(2H)-oxoimidazol-1-yl)-1-piperidinyl]carbonyl]-D-phenylalanyl]-4-(hexahydro-1H-1-azepinyl)-piperidine; and (CJ) 1-[4-amino-3,5-dibromo-N-[[4-(1,3-dihydro-4-(3-thienyl)-2(2H)-oxoimidazol-1-yl)-1-piperidinyl]carbonyl]-D-phenyl-alanyl]-4-(1-methyl-4-piperidinyl)-piperazine, the tautomers, the diastereomers, the enantiomers, the mixtures thereof and the physiologically acceptable salts thereof.

10. The pharmaceutical composition according to claim 6, further comprising one or more inert carriers and/or diluents.

11. The pharmaceutical composition according to claim 7, further comprising one or more inert carriers and/or diluents.

12. The pharmaceutical composition according to claim 8, further comprising one or more inert carriers and/or diluents.

13. The pharmaceutical composition according to claim 9, further comprising one or more inert carriers and/or diluents.

* * * * *